US00PP30610P2

(12) United States Plant Patent
Hoogendoorn

(10) Patent No.: US PP30,610 P2
(45) Date of Patent: Jun. 25, 2019

(54) ***MILTONIDIUM* ORCHID PLANT NAMED 'CAMBIMWIK'**

(50) Latin Name: ***Nothogenus* x *Miltonidium***
Varietal Denomination: CAMBIMWIK

(71) Applicant: ANTHURA B.V., Bleiswijk (NL)

(72) Inventor: Gert-Jan Hoogendoorn, Woubrugge (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,999

(22) Filed: Jun. 7, 2018

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of x *Miltonidium* plant named 'CAMBIMWIK', particularly characterized by having dark red, flecked flowers with a large red-purple and white lip, 1-2 peduncles that are medium long and moderate, leaves that are lanceolate and elongated, and is propagated by meristem tissue culture is disclosed.

3 Drawing Sheets

Genus and species: *Nothogenus*: x *Miltonidium*.
Variety denomination: 'CAMBIMWIK'.

BACKGROUND OF THE NEW PLANT

The present invention comprises a new and distinct cultivar of x *Miltonidium* plant, botanically known as x *Miltonidium* of the Orchidaceae family, and hereinafter referred to by the cultivar name 'CAMBIMWIK'.

*Miltonia, Odontoglossum, Oncidium* and *Brassia* and some other genera are a complex group of orchid species that are easily hybridized. The boundaries between the genera have been under discussion for the last several decades. According to the most recent classification by Pridgeon, Cribb, Chase and Rasmussen (Genera Orchidacearum), the plant herein described is most likely a complex hybrid between *Miltonia* and *Oncidium* species, hence called x *Miltonidium*.

All x *Miltonidium* plants exhibit a sympodial growth habit. The species typically have 4 to 6 leaves per mature pseudobulb: most of the time one lanceolate leaf with an acute apex grown on the apex of the pseudobulb and four leaves grown from the axis at the base (sympodial growth), with two leaves on each side. The peduncles vary in size from 20-90 cm.

x *Miltonidium* orchids are used as flowering potted-plants for home or interiorscape. x *Miltonidium* produces upright or pendant lateral racemes or panicles, often with many showy flowers which open in succession beginning with the lowermost. The flowers possess three sepals and two petals, the lateral ones being alike and having a peculiar labellum. Flower colors include various shades of pink, white, yellow, and red-brown.

x *Miltonidium* orchids are typically propagated from tissue culture. Asexual propagation of x *Miltonidium* is often done from off-shoots which arise from the lower bracts of the inflorescence. The resulting plants are detached from the mother plants and may be planted in a suitable substrate.

The new x *Miltonidium* 'CAMBIMWIK' is particularly characterized by its attractive and unique dark red, flecked flowers with a large red-purple and white lip, economical propagation by tissue culture, early flowering, and a plant dimension suitable for packaging and shipping to the market.

'CAMBIMWIK' is a product of a planned breeding program conducted by the inventor in Bleiswijk, The Netherlands.

The new x *Miltonidium* 'CAMBIMWIK' originated from a cross made by the inventor in July 2004 in Bleiswijk, The Netherlands. The female parent was a red-brown x *Miltonidium* pot plant named '60000-0081' (unpatented) and the male parent was a brown-green *Oncidium* pot plant named '60000-0061' (unpatented). A single plant was selected by the inventor from within the progeny of the stated cross-pollination in a controlled greenhouse in Bleiswijk, The Netherlands in April 2008.

Asexual reproduction of 'CAMBIMWIK' by meristem tissue culture since 2011 in Bleiswijk, The Netherlands has demonstrated that the new variety reproduces true to type with all of the characteristics, as herein described, firmly fixed and retained through successive generations.

Plant Breeder's Rights for this variety have been applied for in Europe on Nov. 27, 2017. 'CAMBIMWIK' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands.

1) Dark red, flecked flowers with a large red-purple and white lip;
2) 1-2 peduncles;

3) Peduncle is medium long and moderate;
4) The shape of the leaf is lanceolate and elongated; and
5) Plants are propagated by meristem tissue culture.

DESCRIPTION OF THE PHOTOGRAPHS

This new x *Miltonidium* plant is illustrated by the accompanying photographs which show the overall plant habit including blooms and foliage of the plant; the colors shown are as true as can be reasonably obtained by conventional photographic procedures. The photographs are of a 70-week old plant grown in a greenhouse in Bleiswijk, The Netherlands in April 2018.

DESCRIPTION OF THE NEW VARIETY

Figure 1:
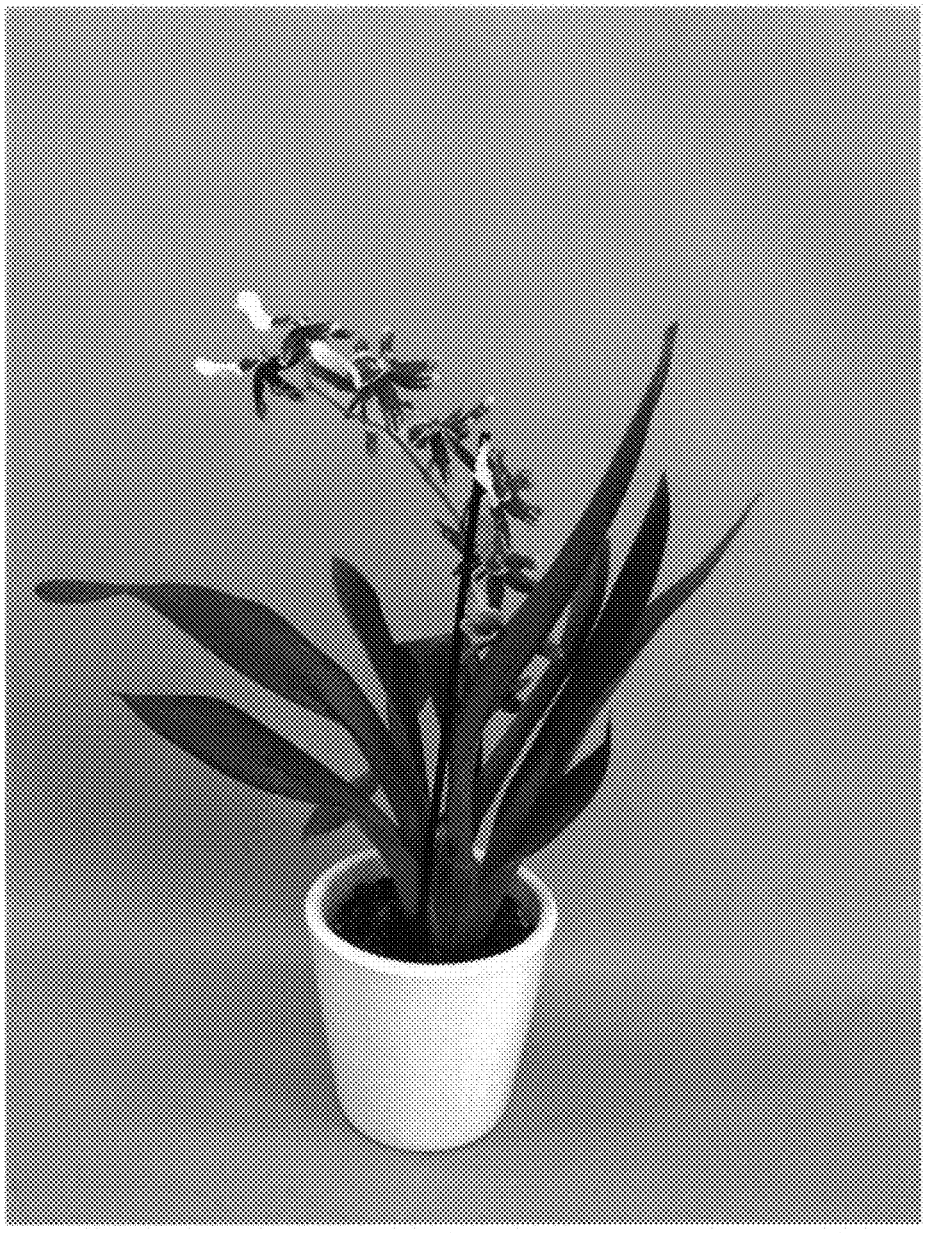
FIG. 1 shows the overall plant habit, including blooms and foliage of 'CAMBIMWIK'.
Figure 2:
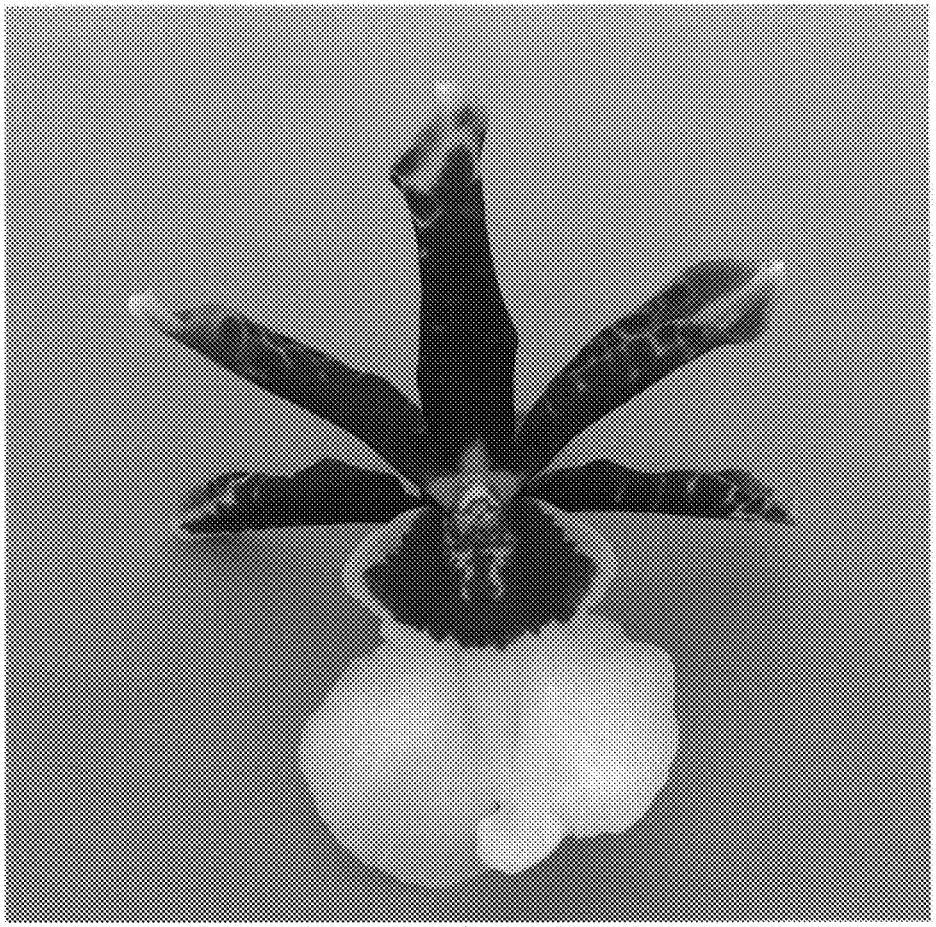
FIG. 2 shows a close-up of a flower of 'CAMBIMWIK'.
Figure 3:
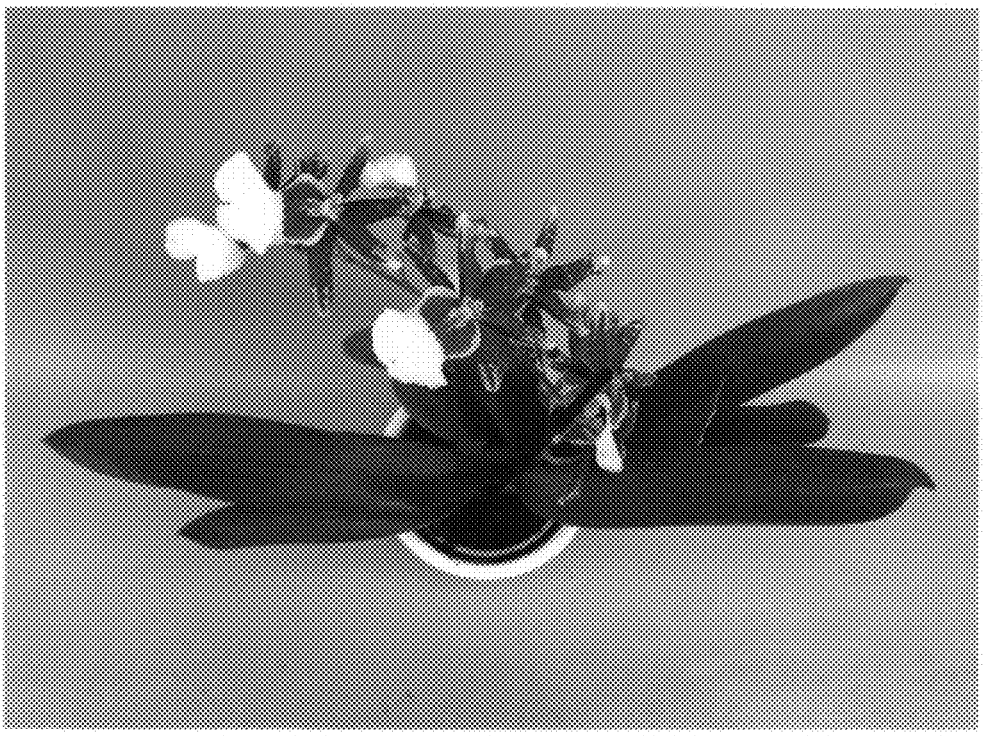
FIG. 3 shows a top view of the leaves and flowers of 'CAMBIMWIK'.

The following detailed description sets forth the distinctive characteristics of 'CAMBIMWIK'. The data which define these characteristics were collected from asexual reproductions carried out in Bleiswijk, The Netherlands. The plant history was taken on 70-week old plants which were planted from tissue culture into 12 centimeter pots, and grown in a greenhouse between 20° C. to 25° C. for 40 weeks. Observations were made in April 2018. Color readings were taken under 4000-6000 lux natural light in the greenhouse. Color references are primarily to The R.H.S. Colour Chart of The Royal Horticultural Society of London (R.H.S.) (2015).

DETAILED BOTANICAL DESCRIPTION

Classification:
- *Family*.—Orchidaceae.
- *Botanical*.—x *Miltonidium*.
- *Common name*.—Cambria.
- *Variety name*.—'CAMBIMWIK'.

Parentage:
- *Female parent*.—x *Miltonidium* cultivar '60000-0081' (unpatented).
- *Male parent*.—*Oncidium* cultivar '60000-0061' (unpatented).

Propagation:
- *Type*.—Meristem tissue culture.

Plant:
- *Crop time* (*time to produce a finished flowering plant*).—50 to 70 weeks for a 12 cm pot.
- *Growth habit of peduncle*.—Standard, green leaves, panicle.
- *Height* (*including pot, including inflorescence*).—40.0 cm to 50.0 cm.
- *Width* (*measured from leaf tips*).—35.0 cm to 40.0 cm.
- *Vigor*.—Moderate.

Roots:
- *Root description*.—Creamy (RHS 158B) colored roots with yellow growing tips (RHS 12A) (The exact shades of white may vary with minimal changes of environmental conditions).

Pseudobulb:
- *Number of pseudobulbs*.—1 to 2.
- *Shape*.—Laterally compressed ovoid.
- *Length*.—5.5 cm to 6.5 cm.
- *Width*.—3.0 cm to 4.0 cm.
- *Thickness*.—1.0 cm to 1.5 cm.
- *Color*.—Green (RHS 146A).

Leaves:
- *Mature leaves*.—Quantity per pseudobulb: 4 to 6 leaves are produced before flowering. Length (fully expanded): 30.0 cm to 35.0 cm. Width: 3.5 cm to 4.5 cm. Shape: Lanceolate. Base shape: Elongated. Apex: Acute. Leaf margin: Entire. Color: Upper surface: RHS 146A. Lower surface: RHS 146B. Texture: Upper surface: Slightly rough. Lower surface: Smooth. Thickness: 0.2 mm to 0.3 mm. Venation: Pattern: Parallel. Color of the midvein: Upper surface: RHS 146A. Lower surface: RHS 146B.

Peduncle:
- *Quantity per plant*.—1 to 2.
- *Number of flowers per peduncle*.—7 to 11.
- *Length*.—From 40.0 cm to 50.0 cm.
- *Diameter*.—4.5 mm to 5.0 mm.
- *Strength*.—Moderate.
- *Aspect*.—Upright.
- *Texture*.—Smooth.
- *Color*.—Green (RHS 146D).
- *Internode length*.—57.0 mm to 62.0 mm.
- *Number of branches*.—0.
- *Callosities*.—None.

Inflorescence description:
- *Appearance*.—Upright, panicle inflorescence with bilaterally symmetrical flowers that open in succession beginning with the lowermost flower.
- *Inflorescence size*.—Height (from base to tip): 230.0 mm to 260.0 mm.
- *Flowering time*.—First flowers can be expected 4 to 6 months after planting in a 12 cm pot.
- *Flower*.—Height: 71.0 mm to 76.0 mm. Diameter: 68.0 mm to 73.0 mm.
- *Flower longevity*.—On the plant: 4 to 7 weeks.
- *Fragrance*.—Present.
- *Petals*.—Shape: Elliptic. Apex: Obtuse. Margin: Undulated. Length (from base to tip): 30.0 mm to 33.0 mm. Width: 13.0 mm to 15.0 mm. Color (when fully opened): Upper surface: Basic color: Dark red (RHS 183A). Over color: Purple-red toward the tip (RHS 186A) and green tip (RHS 145D). Lower surface: Basic color: Green in the middle (RHS 146B). Over color: Dark red edge (RHS 183B) and purple-red toward the tip (RHS 186A).
- *Dorsal sepal*.—Shape: Elliptic. Apex: Obtuse. Margin: Undulated. Length (from base to tip): 33.0 mm to 35.0 mm. Width: 16.0 mm to 18.0 mm. Color (when fully opened): Upper surface: Basic color: Dark red (RHS 183A and 187B). Over color: Purple-red toward the tip (RHS 186B) and very light green tip (RHS 157A). Lower surface: Basic color: Green in the middle (RHS N148C). Over color: Dark red edge (RHS 183B); purple-red toward the tip (RHS 186B) and very light green tip (RHS 157A).
- *Lateral sepals*.—Shape: Elliptic. Margin: Undulated. Length (from base to tip): 33.0 mm to 35.0 mm. Width: 11.0 mm to 13.0 mm. Color (when fully opened): Upper surface: Basic color: Dark red (RHS 183A). Over color: Purple-red toward the tip (RHS 186B) and very light green tip (RHS 157A). Lower surface: Basic color: Green in the middle (RHS 146D). Over color: Dark red edge (RHS 183B) and purple-red toward the tip (RHS 186B).
- *Labellum* (*lip*).—Length: 36.0 mm to 39.0 mm. Width: 33.0 mm to 35.0 mm. Color: Upper surface: Dark red (RHS 187C) at the base and white (RHS 157D)

toward the margin and tip. Lower surface: Diluting dark red (RHS 187B) in the middle and white (RHS 157D) toward the margin. Margin: Undulated.

*Callus*.—Color: Greenish-yellow (RHS 4A/B) with red-brown tips (RHS 177A). Shape: Indescribable. Average size: Indescribable. Average number of protuberance: 3 to 5.

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 4.0 mm to 6.0 mm. Diameter: 3.8 mm to 4.3 mm. Color: Very light green (RHS 157A) with dark purple-pink (RHS 186C) region in the middle and purple-pink margin (RHS N186D). Wings: Absent.

*Cap*.—Average size: 1.0 mm to 3.0 mm. Shape: Oval cup shape. Color: Dark red (RHS 187C).

*Pollinia*.—Quantity: 2. Diameter: 0.6 mm to 0.8 mm. Color: Yellow-orange (RHS 17A).

*Ovary*.—Length: 14.0 mm to 16.0 mm. Diameter: 2.3 mm to 2.5 mm.

*Pedicel*.—Length: 29.0 min, to 32.0 mm. Diameter: 2.0 mm to 2.2 mm. Color: Green (RHS 146D) at the base and dark red (RHS 187A) toward the flower.

Disease, pest, and stress resistance: No specific resistance or susceptibility observed to date.

Temperature tolerance: Not observed to date.

COMPARISON WITH PARENTAL AND SIMILAR VARIETIES

'CAMBIMWIK' differs from female parent '60000-0081' (unpatented) in that 'CAMBIMWIK' has a dark red, flecked flower with a green tip and a dark red and white lip, whereas '60000-0081' has a dark red, even flower and a moderate red and white lip. Additionally, 'CAMBIMWIK' has narrow dorsal and lateral sepals, whereas '60000-0081' has broad dorsal and lateral sepals.

'CAMBIMWIK' differs from male parent '60000-0061' (unpatented) in that 'CAMBIMWIK' has a dark red, flecked flower with a green tip and a dark red and white lip, whereas '60000-0061' has a brown and green, striped flower and a red-purple and white lip.

'CAMBIMWIK' is most similar to the commercial x *Miltonidium* plant named 'CAMBLAJE' (U.S. Plant Pat. No. 29,135) and a x *Miltonidium* plant named 'CAMBLOQA' (U.S. Plant Pat. No. 30,312). 'CAMBIMWIK' differs from commercial variety 'CAMBLAJE' in that 'CAMBIMWIK' has a lip that is dark red at the base and white toward the margin, a greenish-yellow callus with a red-brown tip, and 1 to 2 peduncles per plant, whereas 'CAMBLAJE' has a lip that is dark red at the base and dark pink and white toward the edge, a dark red callus with a yellow tip, and 1 to 3 peduncles per plant.

'CAMBIMWIK' differs from commercial variety 'CAMBLOQA' in that 'CAMBIMWIK' has a greenish-yellow callus with a red-brown tip and 1 to 2 peduncles per plant, whereas 'CAMBLOQA' has a dark red callus with a yellow tip and 1 to 4 peduncles per plant. Additionally, 'CAMBIMWIK' has larger flowers than 'CAMBLOQA'.

I claim:

1. A new and distinct variety of x *Miltonidium* plant named 'CAMBIMWIK', substantially as described and illustrated herein.

* * * * *